(12) United States Patent
Kim et al.

(10) Patent No.: US 12,257,156 B2
(45) Date of Patent: Mar. 25, 2025

(54) ANIMAL KNEE JOINT IMPLANT REFLECTING ANATOMICAL STRUCTURE OF ANIMAL

(71) Applicant: VETRUST MEDITECH CO., LTD., Seoul (KR)

(72) Inventors: Jung-Sung Kim, Daejeon (KR); Jeong-Woo Seo, Seoul (KR); Bo-Kyun Sim, Seoul (KR)

(73) Assignee: Vetrust Meditech Co., Ltd., Seoul (KR)

( * ) Notice: Subject to any disclaimer, the term of this patent is extended or adjusted under 35 U.S.C. 154(b) by 792 days.

(21) Appl. No.: 17/311,057

(22) PCT Filed: Dec. 10, 2019

(86) PCT No.: PCT/KR2019/017413
§ 371 (c)(1),
(2) Date: Jun. 4, 2021

(87) PCT Pub. No.: WO2020/122569
PCT Pub. Date: Jun. 18, 2020

(65) Prior Publication Data
US 2022/0023053 A1    Jan. 27, 2022

(30) Foreign Application Priority Data
Dec. 12, 2018 (KR) .................. 10-2018-0159616

(51) Int. Cl.
*A61F 2/38* (2006.01)
*A61F 2/30* (2006.01)

(52) U.S. Cl.
CPC ........ *A61F 2/3886* (2013.01); *A61F 2/30771* (2013.01); *A61F 2/3836* (2013.01);
(Continued)

(58) Field of Classification Search
CPC .................. A61F 2002/307; A61F 2/3886
See application file for complete search history.

(56) References Cited

U.S. PATENT DOCUMENTS 5,370,701 A * 12/1994 Finn .............. A61F 2/385
623/20.25
5,593,449 A * 1/1997 Roberson, Jr. ...... A61F 2/30749
623/23.15
(Continued)

FOREIGN PATENT DOCUMENTS

| EP | 1506752 A1 * | 2/2005 | ........... A61F 2/3868 |
| JP | 2004-097817 A | 4/2004 | |
| JP | 2017-514589 A | 6/2017 | |

OTHER PUBLICATIONS

International Search Report dated Apr. 1, 2020, issued in PCT Application No. PCT/KR2019/017413, filed Dec. 10, 2019.
(Continued)

*Primary Examiner* — Brian A Dukert
*Assistant Examiner* — Yasniary De La Caridad Morales
(74) *Attorney, Agent, or Firm* — Workman Nydegger

(57) ABSTRACT

The present disclosure relates to an animal knee joint implant that reflects an anatomical structure of an animal. More particularly, the present disclosure relates to an animal knee joint implant that reflects the anatomical structure of an animal, wherein the knee joint implant is capable of being used for diseases, which are accompanied by bone loss, damage to surrounding muscles, ligaments, and the like and are thus more complex than general knee joint diseases such as rheumatoid arthritis and degenerative arthritis, and wherein the animal knee joint implant is capable of reinforcing stability against varus and valgus as well as stability against flexion and extension, and capable of easily complementing gaps that may occur when the bones of a joint are cut.

13 Claims, 14 Drawing Sheets

(52) U.S. Cl.
CPC ............ *A61F 2/3859* (2013.01); *A61F 2/389* (2013.01); *A61F 2002/307* (2013.01); *A61F 2002/3082* (2013.01)

(56) References Cited

U.S. PATENT DOCUMENTS

| | | | |
|---|---|---|---|
| 5,609,643 A | 3/1997 | Colleran et al. | |
| 6,210,443 B1* | 4/2001 | Marceaux | A61F 2/3868 623/20.14 |
| 6,773,461 B2 | 8/2004 | Meyers et al. | |
| 10,070,965 B2 | 9/2018 | Hagen et al. | |
| 2005/0055100 A1 | 3/2005 | Lewis et al. | |
| 2005/0246028 A1* | 11/2005 | Pappas | A61F 2/385 623/20.29 |
| 2008/0051908 A1 | 2/2008 | Angibaud | |
| 2008/0114462 A1* | 5/2008 | Guidera | A61F 2/389 623/20.15 |
| 2008/0161918 A1* | 7/2008 | Fankhauser | A61F 2/38 623/20.14 |
| 2008/0243260 A1* | 10/2008 | Lee | A61F 2/3868 623/20.29 |
| 2009/0299482 A1 | 12/2009 | Metzger et al. | |
| 2012/0109324 A1* | 5/2012 | Keggi | A61B 17/1675 606/88 |
| 2012/0310361 A1* | 12/2012 | Zubok | A61F 2/389 623/20.32 |
| 2018/0206998 A1* | 7/2018 | Fitzpatrick | A61F 2/384 |
| 2019/0142594 A1* | 5/2019 | Yager | A61F 2/4684 623/20.15 |
| 2019/0240032 A1* | 8/2019 | Wasielewski | A61F 2/3859 |

OTHER PUBLICATIONS

Written Opinion dated Apr. 1, 2020, issued in PCT Application No. PCT/KR2019/017413, filed Dec. 10, 2019.

* cited by examiner

ANIMAL KNEE JOINT IMPLANT REFLECTING ANATOMICAL STRUCTURE OF ANIMAL

TECHNICAL FIELD

The present disclosure relates to an animal knee joint implant that reflects the anatomical structure of an animal. More particularly, the present disclosure relates to an animal knee joint implant that reflects the anatomical structure of an animal, wherein the animal knee joint implant is capable of being used for diseases, which are accompanied by bone loss, damage to surrounding muscles, ligaments, and the like and are thus more complex than general knee joint diseases such as rheumatoid arthritis and degenerative arthritis, and wherein the animal knee joint implant is capable of reinforcing stability against varus and valgus as well as stability against flexion and extension, and capable of easily complementing gaps that may occur when the bones of a joint are cut.

BACKGROUND ART

A knee joint refers to a joint formed by a femur, a tibia, and a patella, which are the three bones surrounding a knee, and corresponds to a key joint related to motion using legs, such as walking or running using joint motion and supporting the weight of a person.

An articular cartilage is present at the end of a femur, and a meniscus is present at the end of a tibia. When the cartilage is damaged due to aging, extreme exercise, or the like, bones may come into direct contact with each other, which may cause severe pain.

Knee joint replacement surgery refers to surgery in which a part of the femur and tibia is resectioned and an artificial knee joint implant is inserted instead when such a knee injury occurs.

FIG. 1 is a view illustrating a conventional artificial knee joint implant, which is disclosed in U.S. Pat. No. 5,609,643A (dated Mar. 11, 1997).

Referring to FIG. 1, a conventional artificial knee joint implant 90 includes a tibia element 91 that is inserted into a resected proximal end of a tibia, a bearing element 93 that is seated on the articular surface 91 and provides an articulating surface, and a femur element 95 that is inserted into a resected distal end of a femur to perform joint motion with the bearing element 93.

In general, the tibia element 91 and the femur element 95 are made of a cobalt chromium (CoCr) material, which is a biocompatible metal. The bearing element 93 is made of a polyethylene material so that when the non-metallic bearing element 93 is interposed between the tibia element 91 and the femur element made of metal, smooth joint motion is possible by blocking direct metal-to-metal contact.

However, since the object of implantation of such a conventional artificial knee joint implant 90 is a human being, there is a limitation in that it is impossible to apply the artificial knee joint implant to animals such as dogs, which have an anatomical structure different from that of a human being walking upright.

Despite the number of people with companion animals due to the recent improvement in the standard of living and the trend toward nuclear families, etc., there has been a problem in that, when these animals have knee-related diseases, it is impossible to provide adequate treatment to the animals because there is no dedicated implant to treat the animals.

Therefore, in the related industry, there is a demand for the introduction of a new technology for developing an animal implant that reflects the anatomical structure of an animal such that, even if knee joint replacement surgery is performed on the animal, it is possible to restore the knee joint motion of the animal as it is so that the treated animal is capable of walking normally.

(Patent Document 1) US Patent Publication U.S. Pat. No. 5,609,643A (dated Mar. 11, 1997)

DETAILED DESCRIPTION OF THE INVENTION

Technical Problem

The present disclosure has been conceived in order to solve the problems described above.

In view of the foregoing, an aspect of the present disclosure provides an animal knee joint implant that reflects an anatomical structure of an animal, wherein, even when knee joint replacement surgery is performed on the animal, the knee joint implant allows the knee joint motion of the animal to be restored as it is so that the treated animal is capable of walking normally.

Another aspect of the present disclosure provides an animal knee joint implant that reflects the anatomical structure of an animal, wherein the knee joint implant is capable of being used for diseases, which are accompanied by bone loss, damage to surrounding muscles, ligaments, and the like and are thus more complex than general knee joint diseases such as rheumatoid arthritis and degenerative arthritis.

Another aspect of the present disclosure provides an animal knee joint implant that is capable of implementing a medial proximal portion of a tibia anatomically higher than a lateral proximal portion of the tibia by configuring a seating surface inclined according to the anatomical structure of an animal on a tibia element.

Another aspect of the present disclosure provides an animal knee joint implant that reflects the anatomical structure of an animal, wherein the seating surface of the tibia element is configured to be inclined laterally such that the medial height of the tibia is relatively higher than the lateral height of the tibia.

Another aspect of the present disclosure provides an animal knee joint implant that implements the anatomical structure of a distal portion of a femur of an animal that performs joint motion in the state of being somewhat inclined posteriorly from a proximal portion of a tibia unlike human beings by configuring the seating surface of the tibia element to be inclined posteriorly.

Still another aspect of the present disclosure provides an animal knee joint that reflects the anatomical structure of an animal, wherein a post is configured to protrude on the inclined seating surface of the tibia element and to pass through the bearing element such that the bearing element placed on the seating surface of the tibia element is rotatable about the post.

Still another aspect of the present disclosure provides an animal knee joint implant that reflects the anatomical structure of an animal, wherein a tibia stem is configured to protrude distally from a tibia contact surface of the tibia element such that the tibia element is capable of being stably fixed on a resected proximal portion of the tibia.

Still another aspect of the present disclosure provides an animal knee joint implant that reflects the anatomical structure of an animal, wherein the tibia stem is configured to be inclined posteriorly such that the tibia stem is capable of being easily inserted into the tibia according to the anatomical tibia shape of the animal.

Still another aspect of the present disclosure provides an animal knee joint implant that reflects the anatomical structure of an animal, wherein various bearing elements are capable of being provided according to a gap that may occur when a joint bone is cut such that the gap is capable of being easily complemented.

Still another aspect of the present disclosure provides an animal knee joint implant that reflects an anatomical structure of an animal, wherein a post-receiving hole is configured in the bearing element to receive the protruding post of the tibia element such that the post is inserted into the post-receiving hole, whereby it is possible to prevent the bearing element placed on the inclined seating surface of the tibia element from being separated and it is possible to make the bearing element rotatable about the post.

Still another aspect of the present disclosure provides an animal knee joint implant that reflects the anatomical structure of an animal, wherein the hole axis of the post-receiving hole formed in the bearing element is configured to be perpendicular to a tibia element contact surface of the bearing element so as to provide a joint facet inclined by the inclined angle of the seating surface and to allow a condyle of the femur element to be seated on the inclined joint facet.

Still another aspect of the present disclosure provides an animal knee joint implant that reflects the anatomical structure of an animal, wherein a femur stem is configured on the femur element to protrude so as to be inclined medially such that the femur stem is easily inserted into the medial side of the femur according to the anatomical femur shape of the animal and the femur element is firmly fixed on a resected distal portion of the femur.

[1] Still another aspect of the present disclosure provides an animal knee joint implant that reflects the anatomical structure of an animal, wherein a connecting element is configured to rotatably connect the femur element on the bearing element such that a condyle of the femur element is capable of stably performing joint motion on a joint facet of the bearing element without being separated from the joint facet.

Still another aspect of the present disclosure provides an animal knee joint implant that reflects the anatomical structure of an animal, wherein a yoke unit is configured to be inserted into the separation space between the medial and lateral condyles of the femur element such that a coupling pin is received in a transverse direction, a post is received in a longitudinal direction, and the coupling pin and the post are fastened within the yoke unit, thereby allowing the condyles of the femur element to rotate on the joint facet of the bearing element, and in addition, allowing the bearing element placed on the seating surface of the femur element to rotate about the post.

Still another aspect of the present disclosure provides an animal knee joint implant that reflects the anatomical structure of an animal, wherein the yoke unit receives the coupling pin in the transverse direction and the post in the longitudinal direction, and the coupling pin and the post are fastened in the yoke unit, thereby reinforcing stability against varus and valgus as well as stability against flexion and extension.

Yet another aspect of the present disclosure provides an animal knee joint implant that reflects the anatomical structure of an animal, wherein a coupling pin-receiving hole is configured in the yoke unit such that the femur element is capable of stably rotating about the coupling pin inserted into the coupling pin-receiving hole.

Yet another aspect of the present disclosure provides an animal knee joint implant that reflects the anatomical structure of an animal, wherein a post-receiving hole is configured in the yoke unit such that the post of the tibia element is capable of being received in the post-receiving hole, thereby allowing the bearing element to stably rotate about the post that penetrates the bearing element.

Yet another aspect of the present disclosure provides an animal knee joint implant that reflects the anatomical structure of an animal, wherein the coupling pin-receiving hole and the post-receiving hole communicate with each other such that the coupling pin received in the coupling pin-receiving hole and the post received in the post-receiving hole are capable of being in contact with each other, thereby stably fastening the post and the coupling pin.

Yet another aspect of the present disclosure provides an animal knee joint implant that reflects the anatomical structure of an animal, wherein a gripping groove configured to grip the post is configured on the coupling pin such that, when the post is received through the post-receiving hole in the yoke unit after the coupling pin is received in the coupling pin-receiving hole in the yoke unit, a portion of the received post is engaged in the gripping groove on the coupling pin, thereby preventing the coupling pin from being separated.

Technical Solution

The foregoing aspects are implemented by embodiments configured as follows.

According to an embodiment of the present disclosure, an animal knee joint implant includes a tibia element coupled to a proximal portion of a tibia of an animal, wherein the tibia element includes a seating surface inclined according to the anatomical structure of the animal.

According to another embodiment of the present disclosure, the seating surface is inclined laterally such that a medial height of the tibia element is higher than a lateral height of the tibia element.

According to another embodiment of the present disclosure, the seating surface is inclined posteriorly.

According to another embodiment of the present disclosure, the tibia element includes a post protruding to be perpendicular to the seating surface, and the post is inclined laterally and posteriorly.

According to another embodiment of the present disclosure, the post passes through the bearing element so that the bearing element is rotatable about the post on the seating surface of the tibia element.

According to another embodiment of the present disclosure, the tibia element includes a tibia stem protruding distally from a tibia contact surface.

According to another embodiment of the present disclosure, the tibia stem is inclined posteriorly.

According to another embodiment of the present disclosure, an animal knee joint implant includes a bearing element that is seated on a tibia element and supports a femur element, and the bearing element includes a post-receiving hole configured to receive a post of the tibia element so as to rotate about the post.

According to another embodiment of the present disclosure, the post-receiving hole has a hole axis perpendicular to a tibia element contact surface.

According to another embodiment of the present disclosure, an animal knee joint implant includes a femur element coupled to a distal portion of a femur of an animal, wherein the femur element includes a femur stem protruding to be inclined according to the anatomical structure of the animal.

According to another embodiment of the present disclosure, the femur stem is inclined medially.

According to another embodiment of the present disclosure, an animal knee joint implant includes a tibia element coupled to a proximal portion of a tibia of an animal, a bearing element seated on the tibia element, a femur element coupled to a distal portion of a femur of the animal, and a connecting element configured to rotatably connect the femur element on the bearing element.

According to another embodiment of the present disclosure, the connecting element includes a yoke unit inserted into a separation space between the medial and lateral condyles of the femur element, and a coupling pin configured to pass through and connect the medial and lateral condyles of the femoral element and the yoke unit.

According to another embodiment of the present disclosure, the yoke unit includes a coupling pin-receiving hole configured to receive the coupling pin and a post-receiving hole configured to receive a post of the tibia element.

According to another embodiment of the present disclosure, the coupling pin-receiving hole and the post-receiving hole communicate with each other.

According to another embodiment of the present disclosure, the coupling pin includes a gripping groove configured to grip the post so as to prevent the coupling pin from being separated by the post.

Advantageous Effects

The present disclosure is capable of obtaining the following effects through combinations of the above-described embodiments with configurations to be described below and use relationships therebetween.

According to the present disclosure, it is possible to provide an animal knee joint implant that reflects the anatomical structure of an animal, wherein, even when knee joint replacement surgery is performed on the animal, the knee joint implant allows the knee joint motion of the animal to be restored as it is so that the treated animal is capable of walking normally.

With the present disclosure, it is possible to provide an animal knee joint implant that reflects the anatomical structure of an animal, wherein the knee joint implant is capable of being used for diseases, which are accompanied by bone loss, damage to surrounding muscles, ligaments, and the like and are thus more complex than general knee joint diseases such as rheumatoid arthritis and degenerative arthritis.

With the present disclosure, it is possible to provide an animal knee joint implant that is capable of implementing a medial proximal portion of a tibia anatomically higher than a lateral proximal portion of the tibia by configuring a seating surface inclined according to the anatomical structure of an animal on the tibia element.

With the present disclosure, it is possible to provide an animal knee joint implant that reflects the anatomical structure of an animal, wherein the seating surface of the tibia element is configured to be inclined laterally such that the medial height of the tibia is relatively higher than the lateral height.

With the present disclosure, it is possible to provide an animal knee joint implant that implements the anatomical structure of a distal portion of a femur of an animal that performs joint motion in the state of being somewhat inclined posteriorly from a proximal portion of a tibia unlike human beings by configuring the seating surface of the tibia element to be inclined posteriorly.

With the present disclosure, it is possible to provide an animal knee joint that reflects the anatomical structure of an animal, wherein a post is configured to protrude on the inclined seating surface of the tibia element and to pass through the bearing element such that the bearing element placed on the seating surface of the tibia element is rotatable about the post.

With the present disclosure, it is possible to provide an animal knee joint implant that reflects the anatomical structure of an animal, wherein a tibia stem is configured to protrude distally from a tibia contact surface of the tibia element such that the tibia element is capable of being stably fixed on a resected proximal portion of the tibia.

With the present disclosure, it is possible to provide an animal knee joint implant that reflects the anatomical structure of an animal, wherein the tibia stem is configured to be inclined posteriorly such that the tibia stem is capable of being easily inserted into the tibia according to the anatomical tibia shape of the animal.

With the present disclosure, it is possible to provide an animal knee joint implant that reflects the anatomical structure of an animal, wherein various bearing elements are capable of being provided according to a gap that may occur when a joint bone is cut such that the gap is capable of being easily complemented.

With the present disclosure, it is possible to provide an animal knee joint implant that reflects the anatomical structure of an animal, wherein a post-receiving hole is configured in the bearing element to receive the protruding post of the tibia element such that the post is inserted into the post-receiving hole, whereby it is possible to prevent the bearing element placed on the inclined seating surface of the tibia element from being separated and it is possible to make the bearing element rotatable about the post.

With the present disclosure, it is possible to provide an animal knee joint implant that reflects the anatomical structure of an animal, wherein the hole axis of the post-receiving hole formed in the bearing element is configured to be perpendicular to a tibia element contact surface of the bearing element so as to provide a joint facet inclined by the inclined angle of the seating surface and to allow a condyle of the femur element to be seated on the inclined joint facet.

With the present disclosure, it is possible to provide an animal knee joint implant that reflects the anatomical structure of an animal, wherein a femur stem is configured on the femur element to protrude so as to be inclined medially such that the femur stem is easily inserted into the medial side of the femur according to the anatomical femur shape of the animal and the femur element is firmly fixed on a resected distal femur.

With the present disclosure, it is possible to provide an animal knee joint implant that reflects the anatomical structure of an animal, wherein a connecting element is configured to rotatably connect the femur element on the bearing element such that a condyle of the femur element is capable of stably performing joint motion on a joint facet of the bearing element without being separated from the joint facet.

With the present disclosure, it is possible to provide an animal knee joint implant that reflects the anatomical structure of an animal, wherein a yoke unit is configured to be inserted into the space between the medial and lateral condyles of the femur element such that a coupling pin is received in a transverse direction, a post is received in a longitudinal direction, and the coupling pin and the post are fastened within the yoke unit, thereby allowing the condyles of the femur element to rotate on the joint facet of the bearing element, and in addition, allowing the bearing element placed on the seating surface of the femur element to rotate about the post.

With the present disclosure, it is possible to provide an animal knee joint implant that reflects the anatomical structure of an animal, wherein the yoke unit receives the coupling pin in the transverse direction and the post in the longitudinal direction, and the coupling pin and the post are fastened in the yoke unit, thereby reinforcing stability against varus and valgus as well as stability against flexion and extension.

With the present disclosure, it is possible to provide an animal knee joint implant that reflects the anatomical structure of an animal, wherein a coupling pin-receiving hole is configured in the yoke unit such that the femur element is capable of stably rotating about the coupling pin inserted into the coupling pin-receiving hole.

With the present disclosure, it is possible to provide an animal knee joint implant that reflects the anatomical structure of an animal, wherein a post-receiving hole is configured in the yoke unit such that the post of the tibia element is capable of being received in the post-receiving hole, thereby allowing the bearing element to stably rotate about the post that penetrates the bearing element.

With the present disclosure, it is possible to provide an animal knee joint implant that reflects the anatomical structure of an animal, wherein the coupling pin-receiving hole and the post-receiving hole communicate with each other such that the coupling pin received in the coupling pin-receiving hole and the post received in the post-receiving hole are capable of being in contact with each other, thereby stably fastening the post and the coupling pin.

With the present disclosure, it is possible to provide an animal knee joint implant that reflects the anatomical structure of an animal, wherein a gripping groove configured to grip the post is configured on the coupling pin such that, when the post is received through the post-receiving hole in the yoke unit after the coupling pin is received in the coupling pin-receiving hole in the yoke unit, a portion of the received post is engaged in the gripping groove on the coupling pin, thereby preventing the coupling pin from being separated.

MODE FOR CARRYING OUT THE INVENTION

Hereinafter, embodiments of an animal knee joint implant that reflects anatomical structure of an animal according to the present disclosure will be described in detail with reference to the accompanying drawings. In the following description of the present disclosure, when it is determined that a detailed description of a known function or configuration may unnecessarily make the subject matter of the present disclosure unclear, the detailed description will be omitted. Unless otherwise defined, all terms used herein have the same meaning as the general meaning of the terms understood by a person ordinarily skilled in the art to which this disclosure belongs, and when the general meaning conflicts with the meaning of the terms used herein, the meaning of the terms follows the definition used in the specification. Herein, it is noted that the drawings show an implant inserted in a left leg of an animal and a description thereof is described in order to help understanding.

Figure 1:
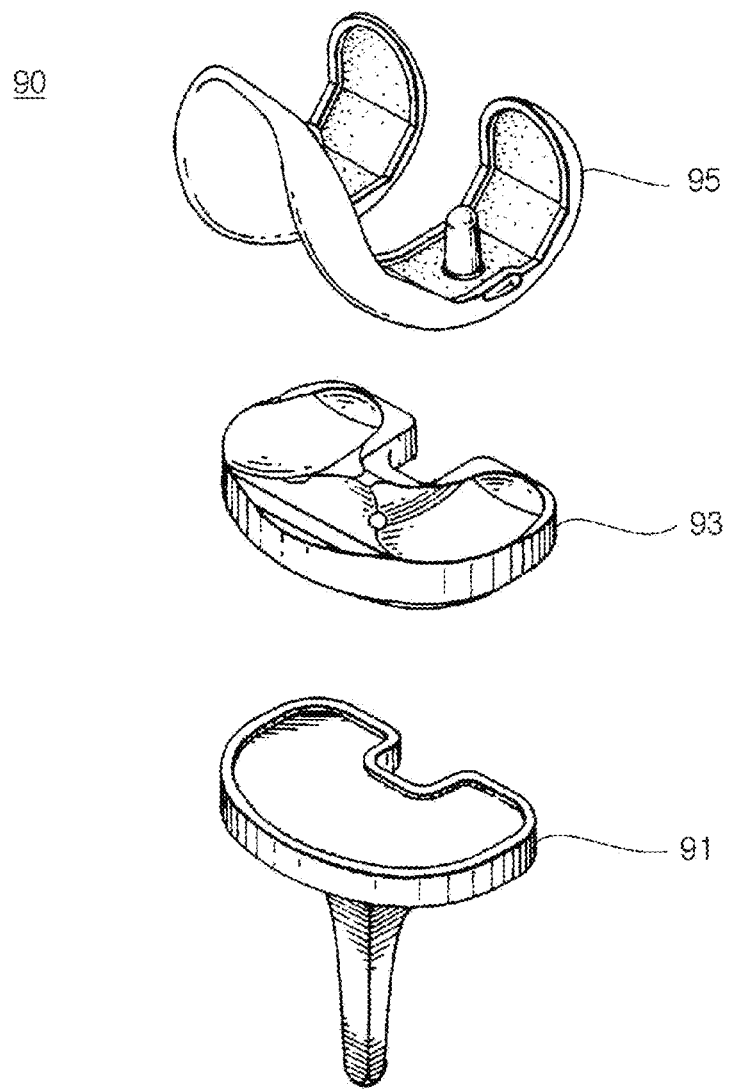
FIG. 1 is a view illustrating a conventional artificial knee joint implant.
Figure 2:
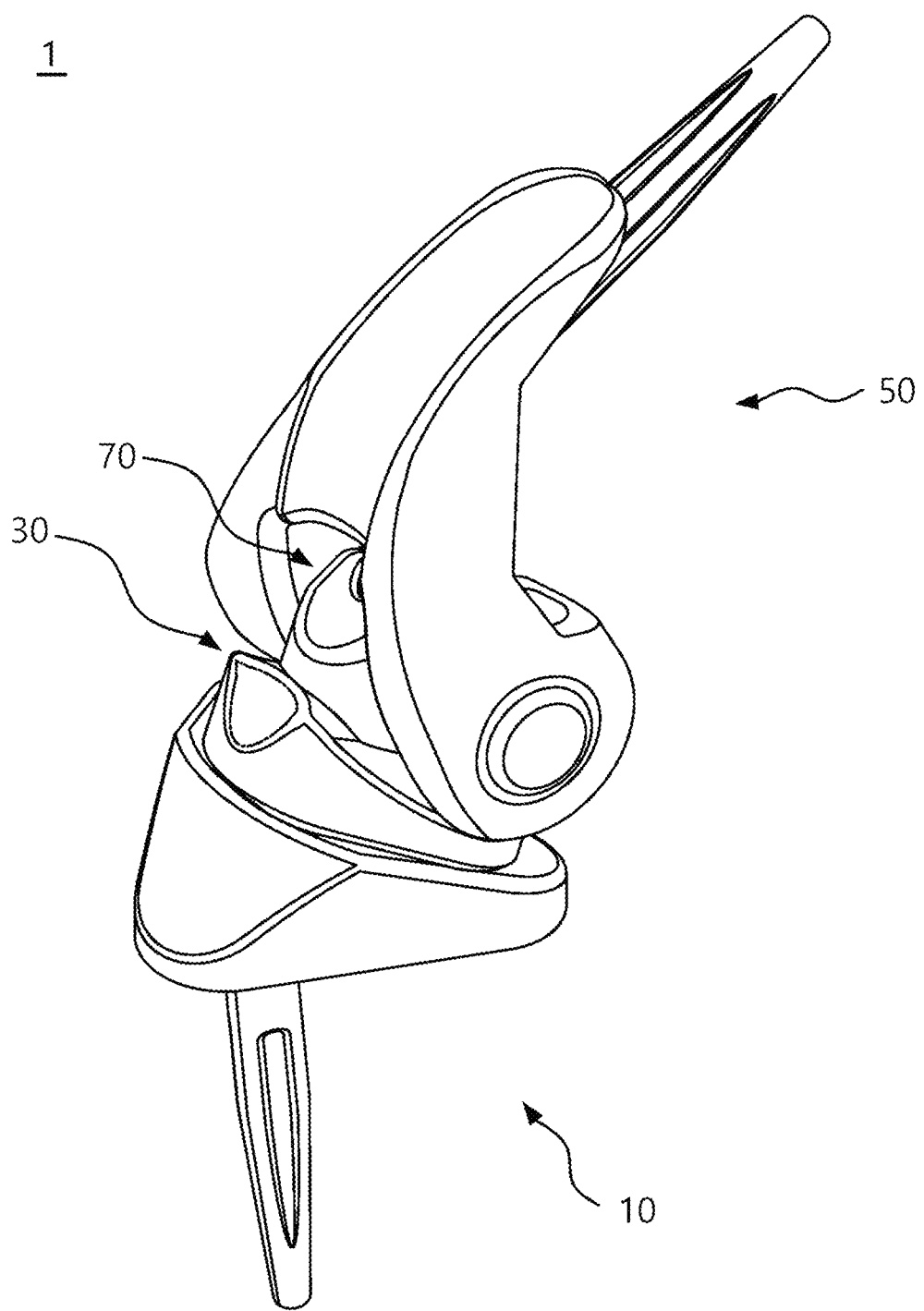
FIG. 2 is a perspective view illustrating an animal knee joint implant according to an embodiment of the present disclosure.
Figure 3:
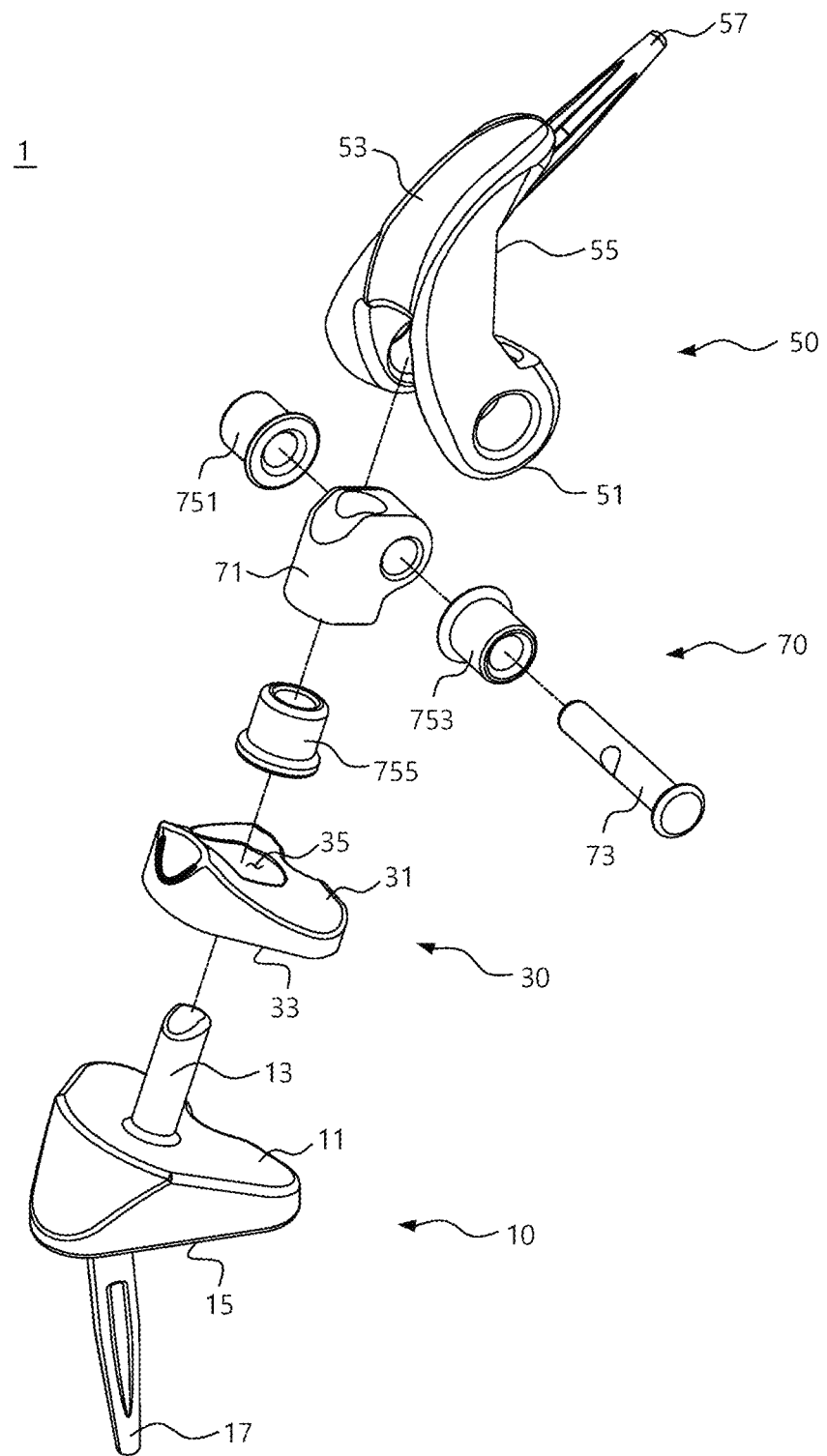
FIG. 3 is an exploded perspective view of FIG. 2.

FIG. 2 is a perspective view illustrating an animal knee joint implant according to an embodiment of the present disclosure, and FIG. 3 is an exploded perspective view of FIG. 2. Referring to FIGS. 2 and 3, an animal knee joint implant 1 of the present disclosure refers to an artificial prosthesis that reflects the anatomical structure of an animal, and that is inserted into a knee joint of the animal so as to replace an anatomical knee joint of the animal damaged by various causes. The term "animal" may be considered to have a broad sense that covers all animals except a human being, such as a dog and a cat. The animal knee joint implant 1 is capable of being used for diseases, which are accompanied by bone loss, damage to surrounding muscles, ligaments, and the like, and are thus more complex than general knee joint diseases such as rheumatoid arthritis and degenerative arthritis. The animal knee joint implant is configured to be capable of reinforcing stability against varus and valgus as well as stability against flexion and extension, and capable of easily complementing gaps that may occur when the bones of a joint are cut. The animal knee joint implant 1 includes a tibia element 10, a bearing element 30, a femur element 50, and a connecting element 70.

Figure 4:
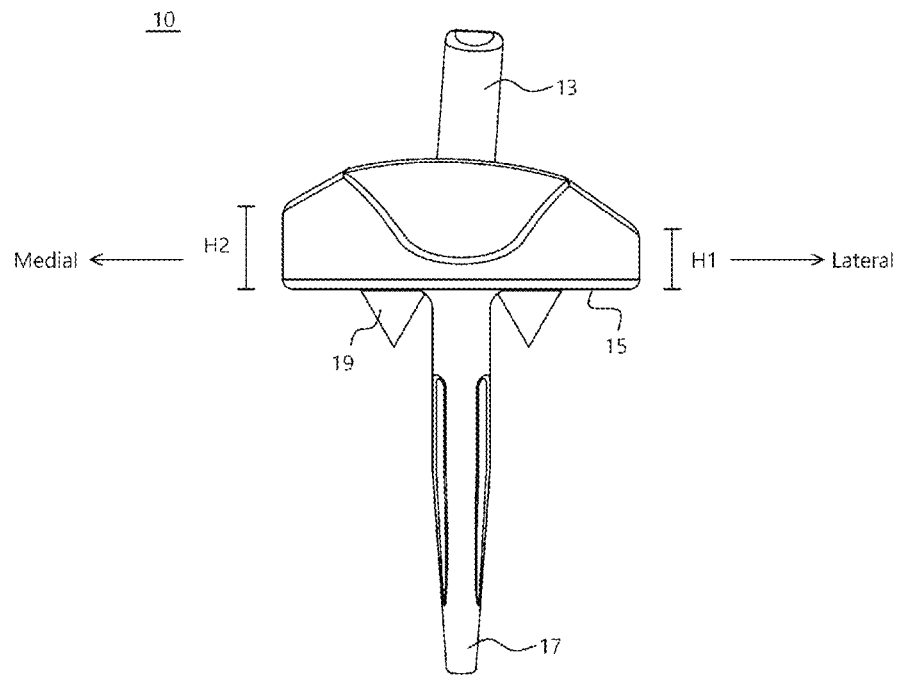
FIG. 4 is a view illustrating a tibia element according to an embodiment of the present disclosure.
Figure 5:
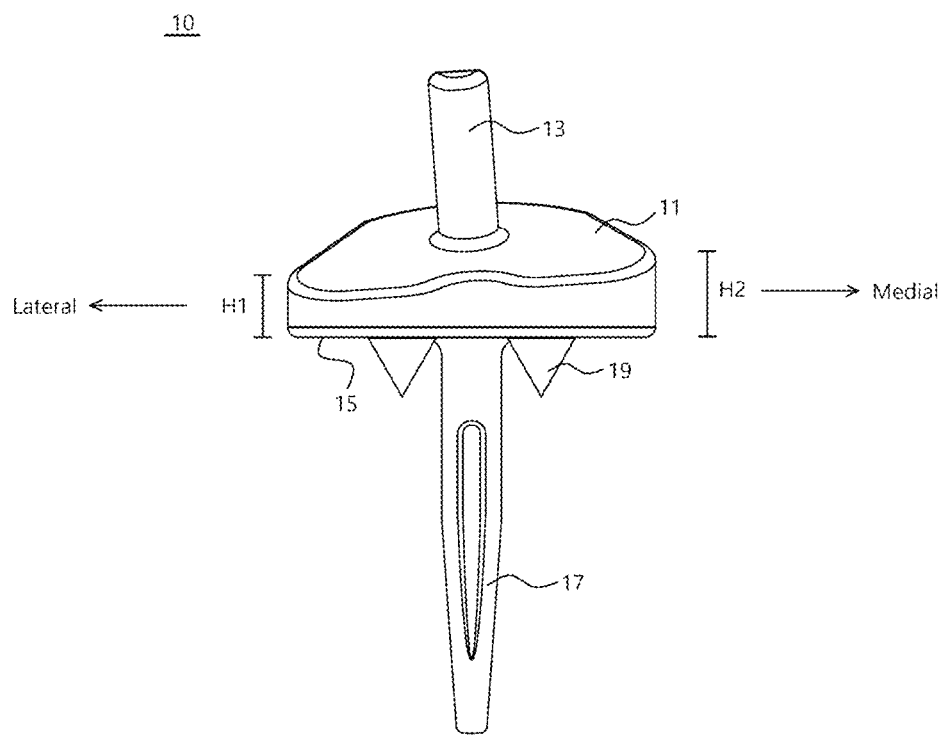
FIG. 5 is a rear view of FIG. 4.
Figure 6:
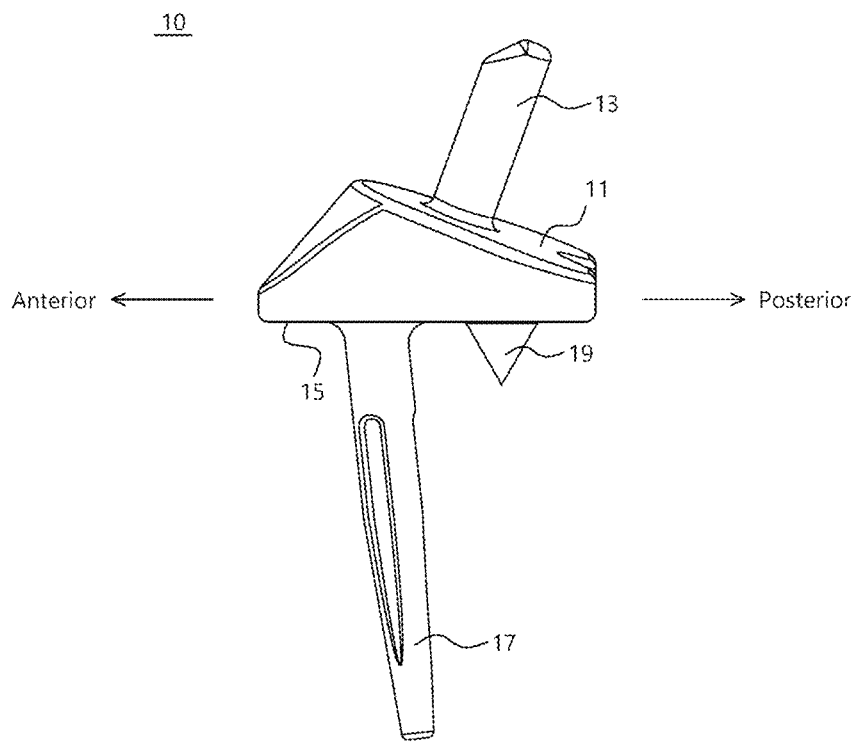
FIG. 6 is a side view of FIG. 4.

The tibia element 10 is a component to be inserted into a tibia of an animal, and provides a space in which the bearing element 30 to be described later is capable of being seated and supports the bearing element 30 to be brought into contact with the femur element 50. The tibia element 10 is horizontally resected by a surgeon in the process of knee joint replacement surgery and placed on the flat proximal portion of an animal's tibia. A portion of the tibia element 10 enters the inside of the animal's cancellous bone so as to allow the tibia element 10 to be stably fixed on the tibia. The tibia element 10 is not limited to a specific concept with respect to the material thereof, but may be preferably made of a cobalt chromium material. FIG. 4 is a view illustrating the tibia element according to an embodiment of the present disclosure, FIG. 5 is a rear view of FIG. 4, and FIG. 6 is a side view of FIG. 4. Referring to FIGS. 4 to 6, the tibia element 10 includes a seating surface 11, a post 13, a tibia contact surface 15, a tibia stem 17, and a tibia spike 19.

The seating surface 11 is a configuration that provides a space in which the bearing element 30, which will be described later, is capable of being seated, and may preferably be configured to be inclined by reflecting the anatomical structure of an animal. Biologically, an animal's tibia has a medial height higher than a lateral height, and the seating surface 11 is preferably configured to be inclined laterally in order to reflect this anatomical structure of an animal. As illustrated in FIGS. 4 and 5, an artificial tibia may be configured to have a medial height H2 relatively higher than a lateral height H1 by configuring the seating surface 11 to be inclined laterally. In addition, unlike biped humans, animals generally perform quadrupedalism. Thus, the distal portion of a femur is not located substantially vertically on the proximal portion of a tibia, but the distal portion of the femur is inclined somewhat posteriorly from the proximal portion of the tibia so as to perform joint motion. Accordingly, as illustrated in FIG. 6, the seating surface 11 may be preferably configured to be inclined laterally and further to be inclined posteriorly. The seating surface 11 is preferably configured as a smooth flat surface such that, when a tibia element contact surface of the bearing element 30 to be described later is supported thereon, the bearing element 30 placed on the seating surface 11 is capable of rotating within a predetermined range.

The post 13 refers to a configuration protruding to be perpendicular to the seating surface 11. The post 13 is not limited to a specific concept with respect to the specific shape thereof, but may preferably have a cylindrical shape, as illustrated in FIGS. 4 to 6. According to the foregoing, the seating surface 11 is configured to be inclined laterally and posteriorly in order to reflect the anatomical structure of an animal. When the post 13 protrudes vertically on the seating surface 11, the post 13 is also configured to be inclined laterally and posteriorly.

The post 13 may be inserted into a post-receiving hole 35 in the bearing element 30 to be described later. The separation of the bearing element 30 from the tibia element 10 is capable of being prevented through the post 13, and the bearing element 30 to be described later is capable of rotating about the post 13 on the seating surface 11 of the tibia element 10.

In addition, the post 13 may be inserted into a post-receiving hole 713 in the yoke unit 71 to be described later. In the yoke unit 71 to be described later, a coupling pin-receiving hole 711 is formed in the transverse direction, and the coupling pin 73 is seated in the coupling pin-receiving hole 711. A gripping groove 731 is formed on the seated coupling pin 73. When the post 13 is inserted into the post-receiving hole 713 after the coupling pin 73 is inserted into the coupling pin-receiving hole 711, a portion of the post 13 is engaged in the gripping groove 731 in the coupling pin 73 so that it is possible to prevent separation of the coupling pin 73.

The tibia contact surface 15 refers to a portion of the tibia element 10 that directly comes into contact with the tibia. In knee joint replacement surgery, a process of horizontally resecting the proximal portion of a problematic tibia is performed. In order for the tibia element 10 to be stably seated on the horizontally resected proximal portion of the tibia, the tibia contact surface 15 is preferably configured to have a shape complementary to the surface of the horizontally resected proximal portion of the tibia, as illustrated in FIG. 6.

The tibia stem 17 refers to a configuration protruding distally from the tibia contact surface 15. In the process of seating the tibia element 10 on the resected proximal portion of the tibia, it is necessary not only to position the tibia element at a predetermined point, but also to stably fix the tibia element 10 on the proximal portion of the tibia so as to prevent the tibia element 10 from deviating from the corresponding position. Therefore, the tibia stem 17 is inserted into the tibia and functions to firmly fix the tibia element 10 to the tibia. Preferably, the tibia stem 17 may be configured to be inclined posteriorly along the anatomical tibia shape of the animal such that the tibia step 17 is capable of being inserted into the cancellous bone of the tibia, which has relatively weak strength. The tibia stem 17 is not limited to any specific concept with respect to the specific shape thereof, but may have a substantially cylindrical shape, as illustrated in FIG. 6.

The tibia spike 19 refers to a configuration that protrudes distally at a point of the tibia contact surface 15 that does not interfere with the tibia stem 17 in order to secure the force of fixing the tibia element 10. When it is difficult to secure a sufficient fixation force between the tibia element 10 and the tibia only with the tibia stem 17, the tibia spike 19 is configured on the tibia contact surface 15 so as to increase the structural stability of the tibia element 10 inserted into the proximal portion of the tibia. The tibia spike 19 is not limited to any specific concept with respect to the shape thereof, but preferably, as illustrated in FIG. 6, the distal end thereof may be configured in a sharp cone shape. In addition, a plurality of tibia spikes 19 may be provided in a portion having weak structural stability. In addition, the tibia stem 17 is configured to be inclined posteriorly so as to conform to the anatomical structure of an animal. However, the tibia spike 19 complements the fixation force of the tibia stem 17, and the degree of protrusion of the tibia spike 19 from the tibia contact surface 15 is shorter than that of the tibia stem 17. Thus, the tibia spike 19 may be formed to protrude vertically from the tibia contact surface 15 without being inclined.

Figure 7:
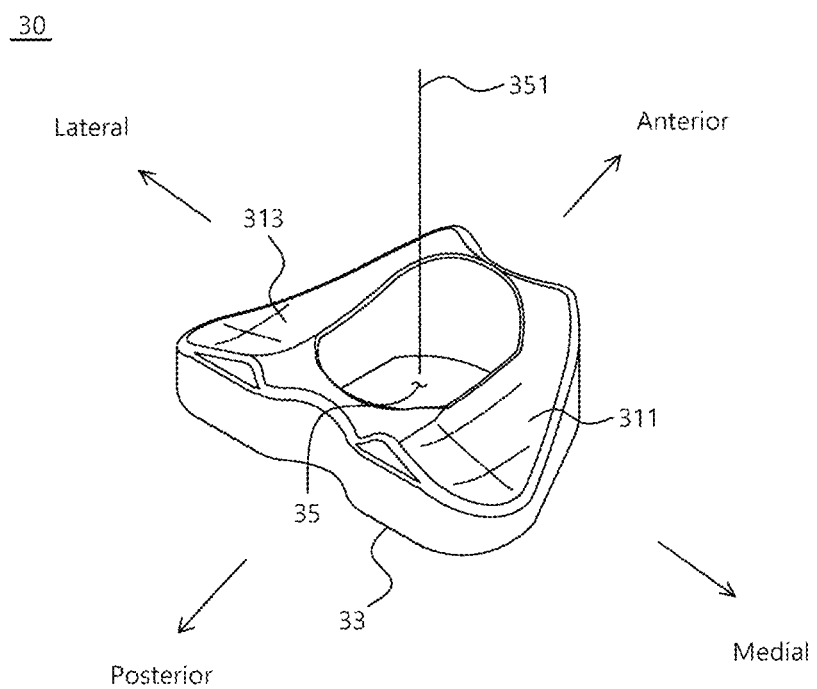
FIG. 7 is a view illustrating a bearing element according to an embodiment of the present disclosure.
Figure 8:
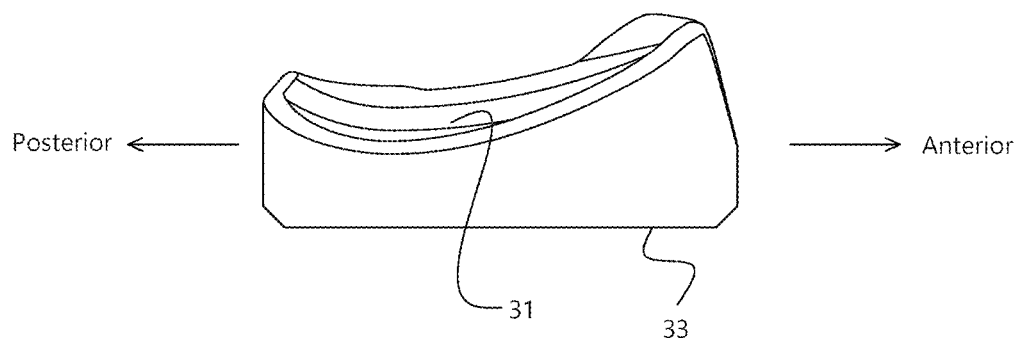
FIG. 8 is a side view of FIG. 7.
Figure 9:
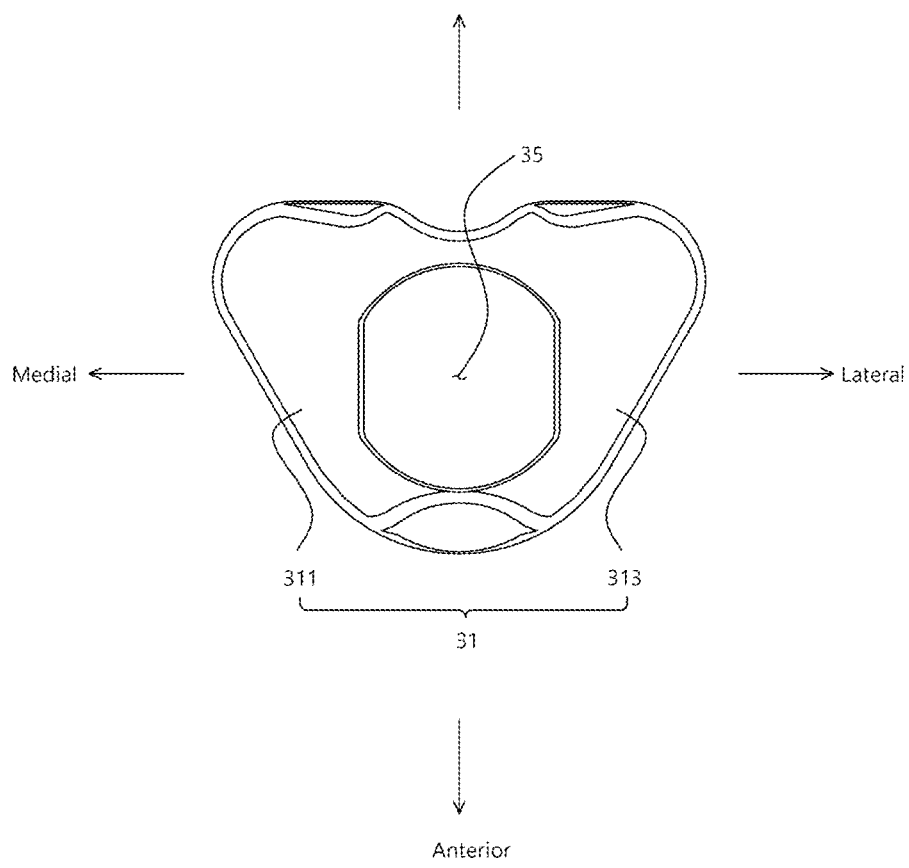
FIG. 9 is a plan view of FIG. 7.
Figure 10:
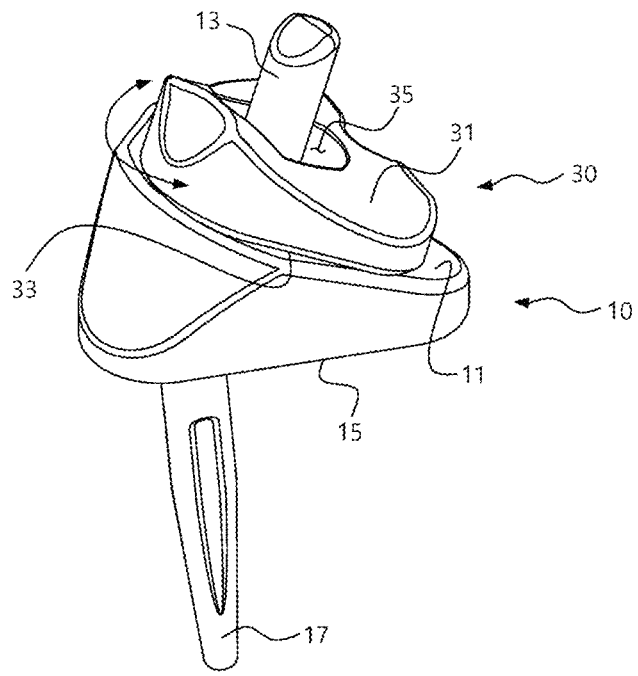
FIG. 10 is a view illustrating the bearing element seated on the tibia element.

FIG. 7 is a view illustrating a bearing element according to an embodiment of the present disclosure, FIG. 8 is a side view of FIG. 7, FIG. 9 is a plan view of FIG. 7, and FIG. 10 is a view illustrating the bearing element seated on the tibia element. Hereinafter, reference will be made to FIGS. 7 to 10.

The bearing element 30 refers to a configuration that is seated on the tibia element 10 and supports the femur element 50 to be described later. On the bearing element 30, a medial condyle 511 and a lateral condyle 513 of the femur element 50, which will be described later, are seated to perform knee joint motion. The bearing element 30 is not limited to a specific concept with respect to the material thereof, but may be preferably made of a polyethylene material. When the bones of a joint are cut, gaps may occur, and these gaps may have various shapes. The bearing element may be provided in various forms according to the gaps, and through this, the gaps may be easily complemented. The bearing element 30 includes a joint facet 31, a tibia element contact surface 33, and a post-receiving hole 35.

The joint facet 31 is a portion that is in contact with the medial condyle 511 and the lateral condyle 513 of the femur element 50, and is configured to have a concave shape so as to receive the condyles of the femur element 50 having a convex shape. The joint facet 31 is divided into a medial joint facet 311 configured to receive the medial condyle 511 of the femur element 50 and a lateral joint facet 311 configured to receive the lateral condyle 513 of the femur element 50. Preferably, the medial joint facet 311 and the lateral joint facet 313 may be symmetrical to each other.

The tibia element contact surface 33 refers to a portion of the bearing element 30 that is in contact with the seating surface of the tibia element 10. As described above, the seating surface 11 is configured as a smooth flat surface in order to facilitate the support of the bearing element 30 and rotation of the bearing element 30 about the post 13. Preferably, the tibia element contact surface 33 is also configured as a smooth flat surface.

The post-receiving hole 35 is configured to receive the post 13 of the tibia element 10, and refers to a hole penetrating from the joint facet 31 to the tibia element contact surface 33. The bearing element 30 is prevented from deviating from the seating surface 11 of the tibia element 10 by the post 13 inserted into the post-receiving hole 35, and the bearing element 30 is capable of rotating about the post 13, as illustrated in FIG. 10. The post-receiving hole 35 is preferably configured such that the hole axis 351 thereof is perpendicular to the tibia element contact surface 33 so as to accommodate the post 13 protruding vertically from the seating surface 11.

Figure 11:
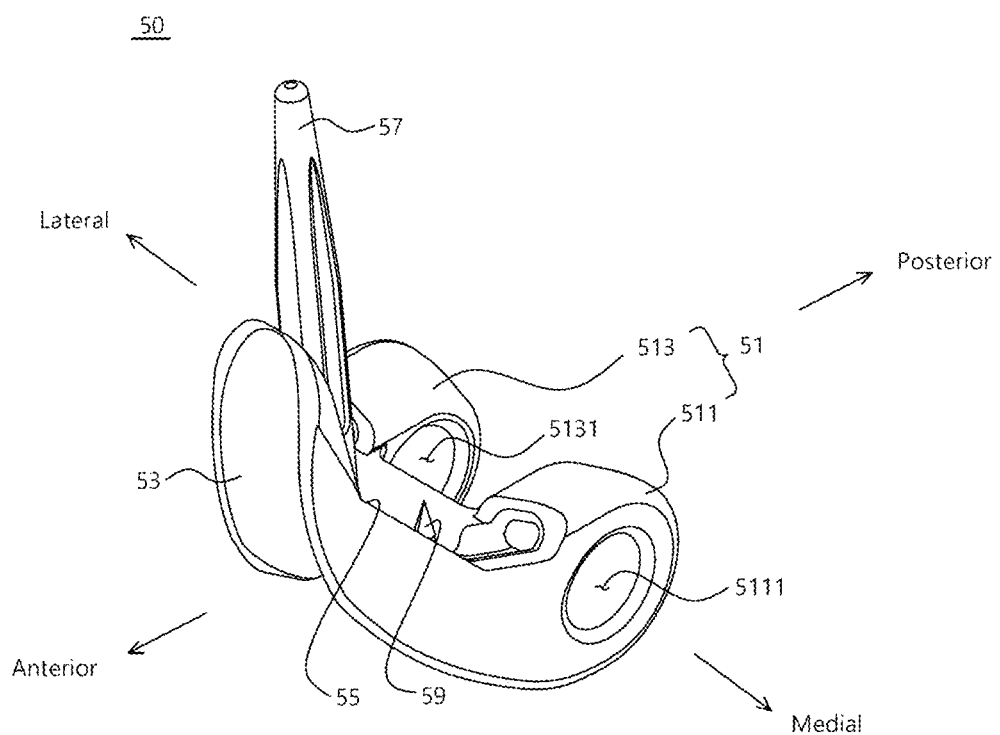
FIG. 11 is a view illustrating a femur element according to an embodiment of the present disclosure.
Figure 12:
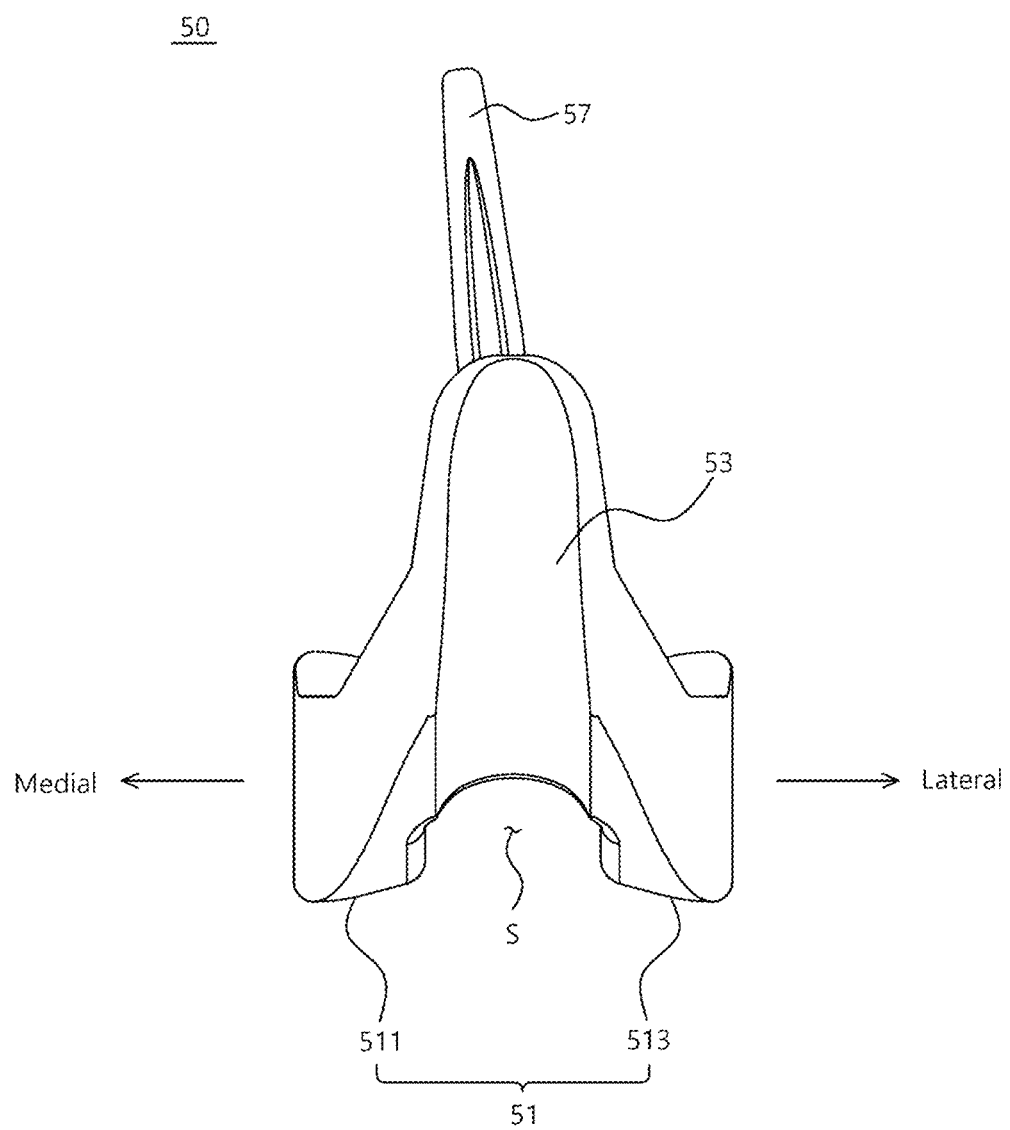
FIG. 12 is a front view of FIG. 11.
Figure 13:
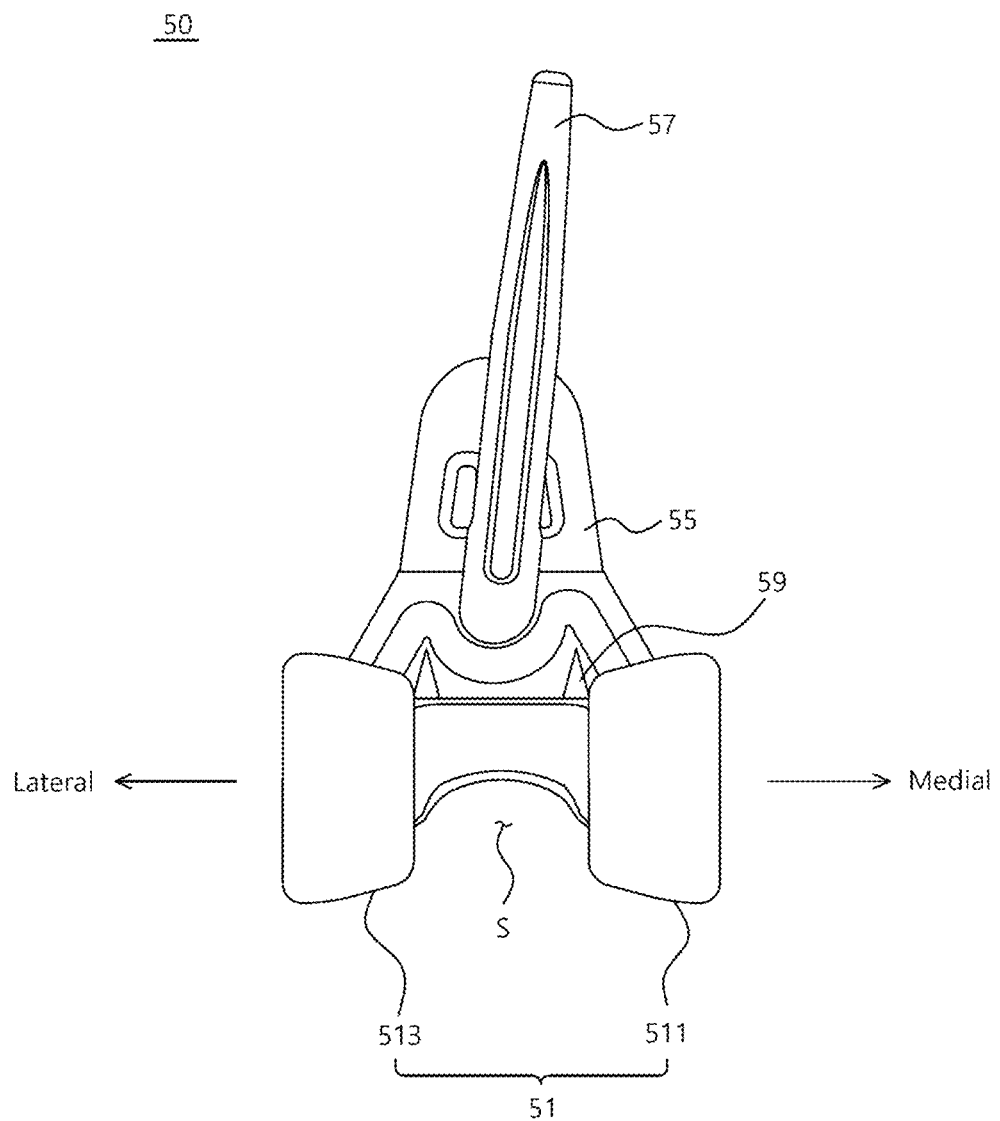
FIG. 13 is a rear view of FIG. 11.
Figure 14:
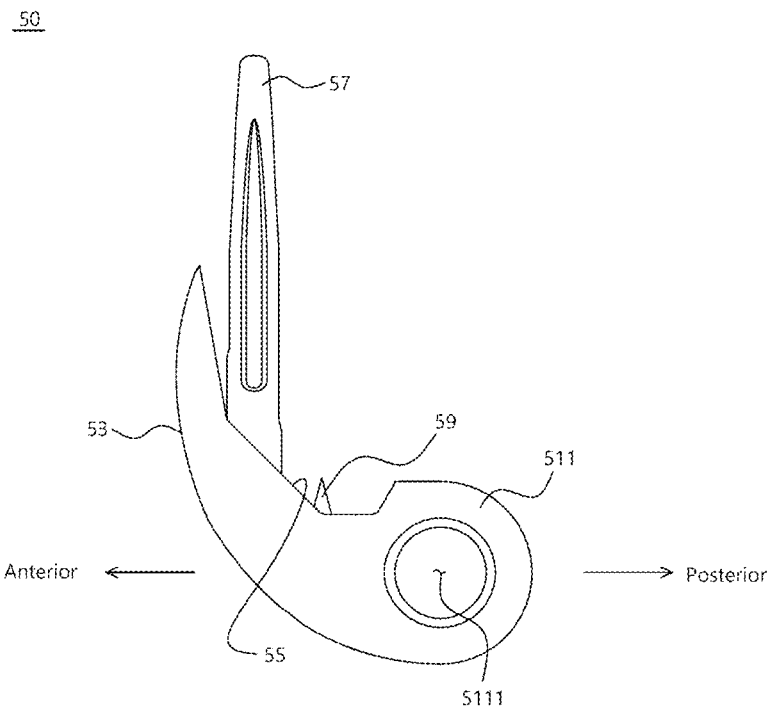
FIG. 14 is a side view of FIG. 11.

FIG. 11 is a view illustrating a femur element according to an embodiment of the present disclosure, FIG. 12 is a front view of FIG. 11, FIG. 13 is a rear view of FIG. 11, and FIG. 14 is a side view of FIG. 11. Hereinafter, reference will be made to FIGS. 11 to 14.

The femur element 50 is configured to be inserted into a femur of an animal, and is preferably coupled to the distal end of the femur. The femur element 50 is in contact with the joint facet 31 of the bearing element 30 so as to perform joint motion. The femur element 50 is not limited to a specific concept with respect to the material thereof, but may be preferably made of a cobalt chromium material. The femur element 50 includes condyles 51, a pulley portion 53, a femur contact surface 55, a femur stem 57, and a femur spike 59.

The condyles 51 are portions having a convex shape on the lower side of the femur element 50, and are configured to perform joint motion while being in contact with the joint facet 31 of the bearing element 30 having a concave shape. The condyles 51 are divided into a medial condyle 511 and a lateral condyle 513 while forming a separation space S therebetween. The medial condyle 511 and the lateral condyle 513 are seated on the medial joint facet 311 and the lateral joint facet 313, respectively, so as to perform joint motion. Preferably, the medial condyle 511 and the lateral condyle 513 may be configured to be symmetrical to each other.

In each condyle 51, a hole may be configured to penetrate the condyle 51 from the medial surface to the lateral surface of the condyle 51. The hole penetrating the medial condyle 511 from the medial surface to the lateral surface of the medial condyle 511 is referred to as a medial coupling pin-seating hole 5111, and the hole penetrating the lateral condyle 513 from the medial surface to the lateral surface of the lateral condyle 513 is referred to as a lateral coupling pin-seating hole 5131. The medial coupling pin-seating hole 5111 and the lateral coupling pin-seating hole 5131 receive a coupling pin 73 to be described later so that the femur element 50 is rotatable about the coupling pin 73.

The pulley portion 53 is formed on the anterior side of the femur element 50 and configured to be in contact with a patella of an animal for knee joint replacement surgery.

The femur contact surface 55 refers to a surface of the femur element 50 that is in contact with the femur, and may preferably be formed on the rear surface of the pulley portion 50.

The femur stem 57 refers to a configuration that protrudes proximally from the femur contact surface 55. The femur stem 57 is not limited to any specific concept with respect to the specific shape thereof, but may preferably have a substantially cylindrical shape. The femur stem 57 is inserted into the femur such that the femur element 50 is capable of being firmly fixed to the femur of the animal while having structural stability. Preferably, the femoral stem 57 may be configured to be inclined medially to reflect the anatomical structure of an animal.

Figure 15:
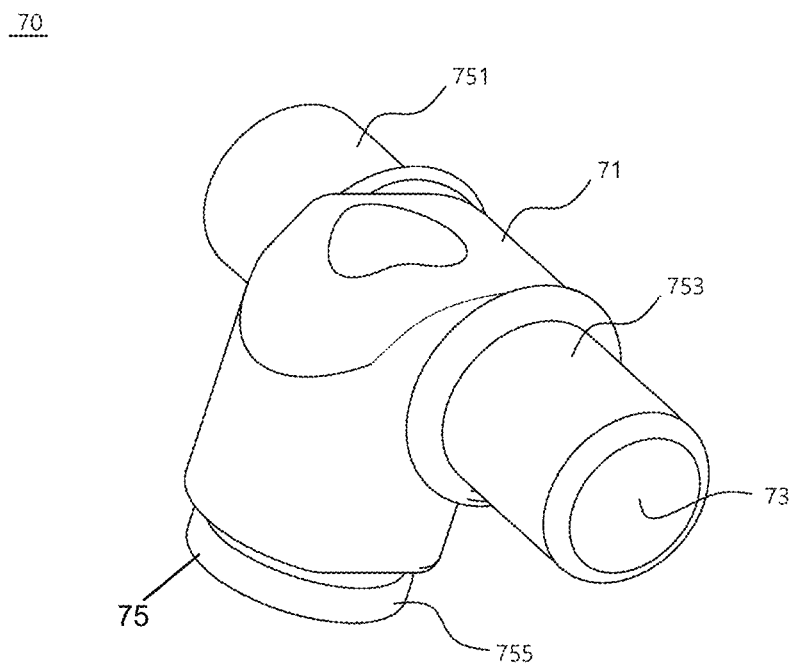
FIG. 15 is a view illustrating a connecting element according to an embodiment of the present disclosure.

The connecting element 70 refers to a configuration that enables joint motion between the femur element 50 and the bearing element 30. Specifically, the connecting element 70 is connected to the medial condyle member 511 and the lateral condyle 513 of the femur element 50 so as to designate the center of rotation of the condyles 51, and receives the post 13 of the tibia element 10 that penetrates the element 30 so as to connect the bearing element 30. As a result, the connecting element 70 is capable of connecting the tibia element 10 and the femur element 50 to each other while preventing the bearing element 30 interposed between the tibia element 10 and the femur element 50 from deviating from the bearing element 30 so as to allow the femur element 50 to stably perform joint motion on the joint surface 31 of the bearing element 30. FIG. 15 is a view illustrating a connecting element according to an embodiment of the present disclosure. Referring to FIG. 15, the connecting element 70 includes a yoke unit 71, a coupling pin 73, and a bushing unit 75.

Figure 16:
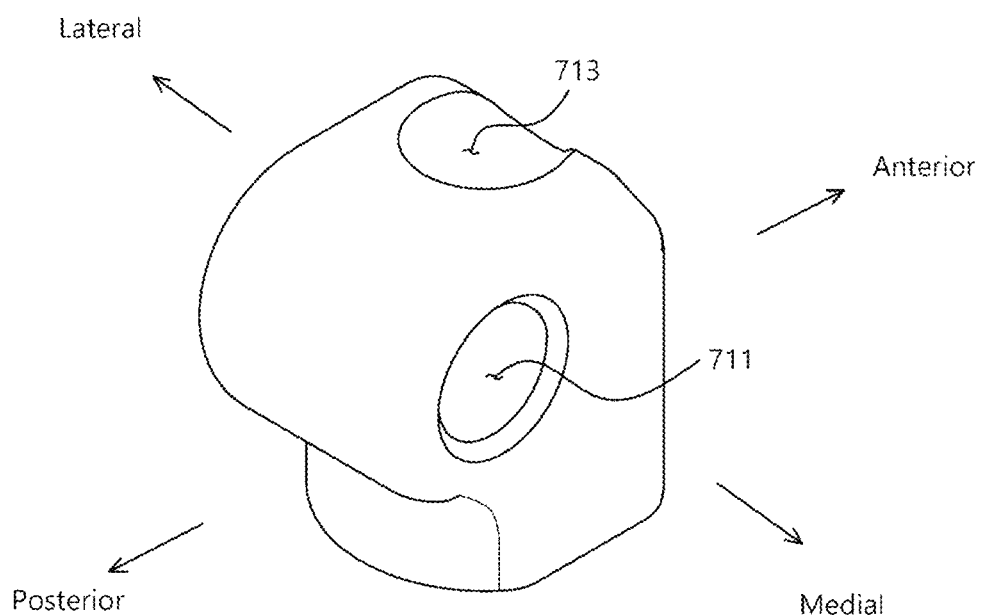
FIG. 16 is a view illustrating a yoke unit according to an embodiment of the present disclosure.
Figure 17:
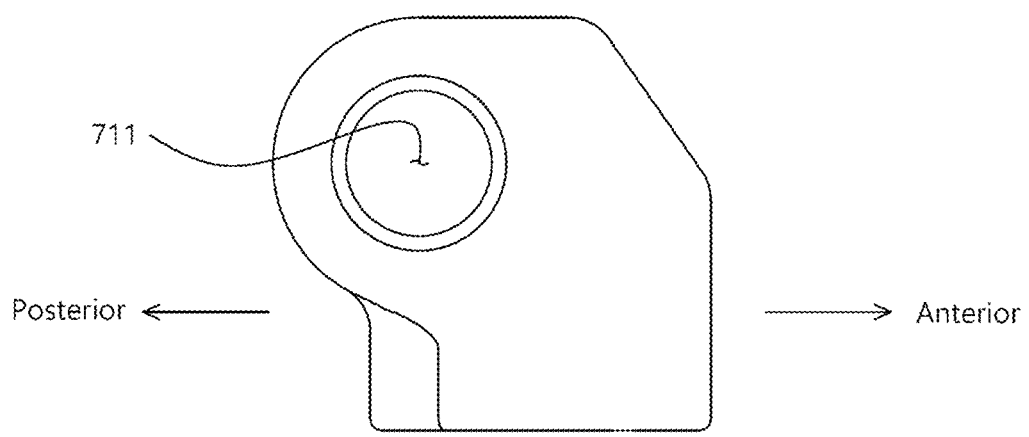
FIG. 17 is a side view of FIG. 16.
Figure 18:
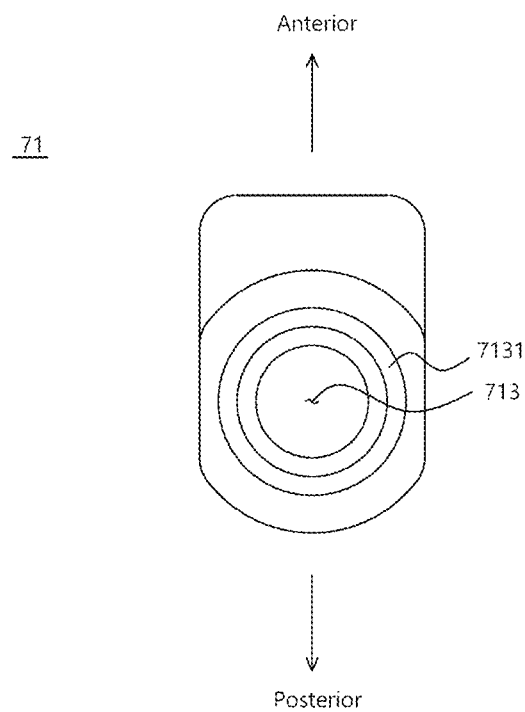
FIG. 18 is a bottom view of FIG. 16.

FIG. 16 is a view illustrating a yoke unit according to an embodiment of the present disclosure, FIG. 17 is a side view of FIG. 16, and FIG. 18 is a bottom view of FIG. 16. Hereinafter, reference will be made to FIGS. 16 to 18.

The yoke unit 71 is a configuration that is inserted into a separation space S between the medial condyle 511 and the lateral condyle 513 of the femur element 50, and may be preferably configured to have a shape complementary to the medial space shape of the separation space S. The yoke unit 71 is configured to receive the post 13 of the tibia element 10 and to receive a coupling pin 73 to be described later. The post 13 may be received through the lower surface of the yoke part 71, and the coupling pin 73 may be received through the medial and lateral surfaces of the yoke unit 71. As will be described later, a gripping groove 731 is formed on the coupling pin 73 so that the post 13 is engaged in the gripping groove 731. For this purpose, the yoke unit 71 preferably receives the post 13 after receiving the coupling pin 73 therein. The yoke unit 71 is not limited with respect to the material thereof, but may be made of a biometallic material in order to secure the strength of the connecting portion. The yoke unit 71 includes a coupling pin-receiving hole 711 and a post-receiving hole 713.

The coupling pin-receiving hole 711 is configured to receive the coupling pin 73 to be described later, and may have a shape that penetrates the yoke unit 71 from the medial surface to the lateral surface, as illustrated in FIG. 17. In addition, the coupling pin-receiving hole 711 is preferably configured to have a shape complementary to the outer circumferential shape of the coupling pin 73 for easy seating of the coupling pin 73. The coupling pin-receiving hole 711 may communicate with the post-receiving hole 713 to be described later. As a result, the coupling pin 73 received in the coupling pin-receiving hole 711 is capable of being engaged with the post 13 received in the post-receiving hole 713.

The post-receiving hole 713 is configured to receive the post 13 of the tibia element 10, and may have a shape that penetrates the yoke unit 71 from the bottom surface to the top surface, as illustrated in FIG. 18. For easy insertion of the post into the post-receiving hole 713, the post-receiving hole 713 may be configured to have a shape complementary to the outer circumferential shape of the post 13. However, as described above, when the tibia element 10 and the yoke unit 71 are made of a metal material, metals come into contact with each other. Thus, since a lower bushing 755 to be described later may be interposed between the post-receiving hole 713 and the post 13, it is more preferable to configure the inner space of the post-receiving hole 713 in a shape complementary to the outer circumferential shape formed by fitting the lower bushing 755 on the post 13. In this case, as illustrated in FIG. 18, the post-receiving hole 713 may have a stepped portion 7131 on which one end of the lower bushing 755 is seated.

Figure 19:
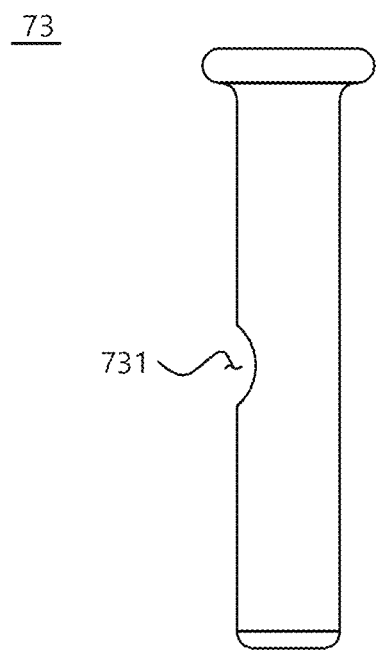
FIG. 19 is a view illustrating a coupling pin according to an embodiment of the present disclosure.

The coupling pin 73 is configured to penetrate and connect the medial condyle 511, the lateral condyle 513, and the yoke unit of the femur element 50, and functions as the center axis of rotation of the femur element 50 to perform joint motion on the joint facet 31 of the bearing element 30. The coupling pin 73 is not limited to a specific concept with respect to the shape thereof, but may preferably be configured in a cylindrical shape having a circular cross section in order to induce smooth joint motion. FIG. 19 is a view illustrating a coupling pin according to an embodiment of the present disclosure. Referring to FIG. 19, the coupling pin 73 includes a gripping groove 731.

The gripping groove 731 is configured to grip the post 13 of the tibia element 10, and refers to a portion recessed on the coupling pin 73 while having a shape complementary to the outer circumferential surface of the post 13. The coupling pin 73 passes through the medial coupling pin-seating hole 5111 of the medial condyle 511 and the lateral coupling pin-seating hole 5131 of the lateral condyle 513. When there is no separate means for fixing the coupling pin 73, the coupling pin 73 may be separated from the predetermined position through the medial coupling pin-seating hole 5111 or the lateral coupling pin-seating hole 5131. Therefore, in order to prevent such a problem, by configuring the gripping groove 731 on the coupling pin 73 so that the post 13 is seated in the gripping groove 731, it is possible to prevent the coupling pin 73 from deviating medially or laterally.

Figure 20:
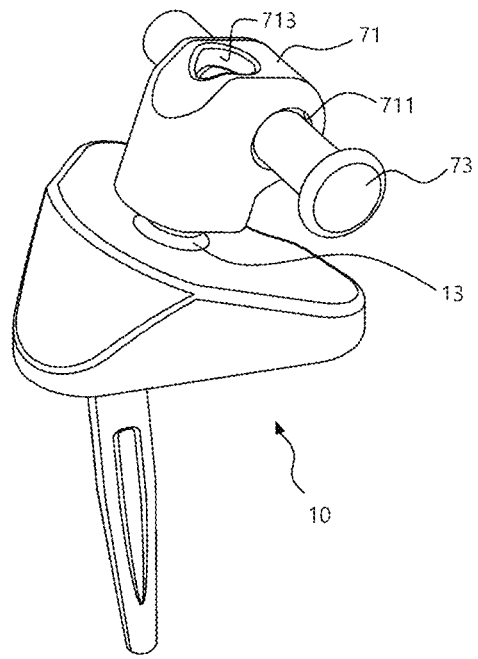
FIG. 20 is a view illustrating the post and the coupling pin inserted into the yoke unit.
Figure 21:
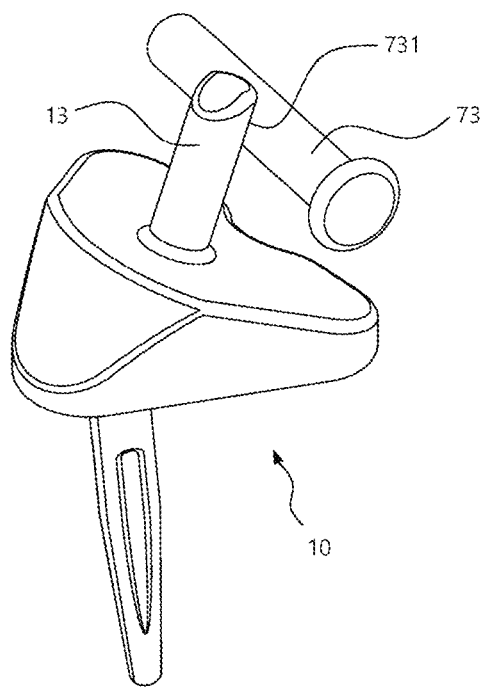
FIG. 21 is a view illustrating the state in which the post and the coupling pin of FIG. 20 are coupled.
Figure 22:
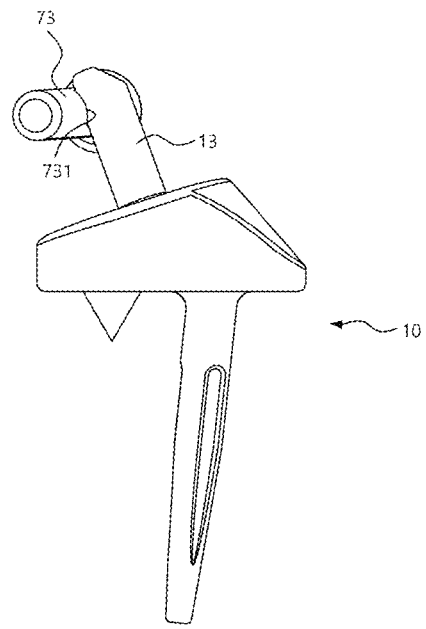
FIG. 22 is a view illustrating the state in which the post and the coupling pin of FIG. 20 are coupled.

FIG. 20 is a view illustrating the post and the coupling pin inserted into the yoke unit, and FIGS. 21 and 22 are views illustrating the state in which the post and the coupling pin of FIG. 20 are coupled. Referring to FIGS. 20 to 22, as described above, it can be seen that a portion of the post 13 of the tibia element 10 enters the gripping groove 731 in the coupling pin 73 and the position of the coupling pin 73 is fixed by the post 13. In this way, since the yoke unit 71 receives the coupling pin 73 in the transverse direction and the post 13 in the longitudinal direction, and the coupling pin 73 and the post 13 are fastened in the yoke unit 71, it is possible to further reinforce stability against varus and valgus as well as stability against flexion and extension.

The bushing unit 75 refers to a configuration of a non-metal material interposed between components, each made of a metal material, to prevent direct contact between the metal materials. Each of the tibia element 10, the femur element 50, the yoke unit 71, and the coupling pin 73 may be made of a biometallic material to express predetermined strength. The medial bushing 751 may be inserted into the medial coupling pin-seating hole 5111 in the medial condyle 511, the lateral bushing 753 may be inserted into the lateral coupling pin-seating hole 5131 in the lateral condyle 513, and the lower bushing 755 may be inserted into the post-receiving hole 713 in the yoke unit 71.

Figure 23:
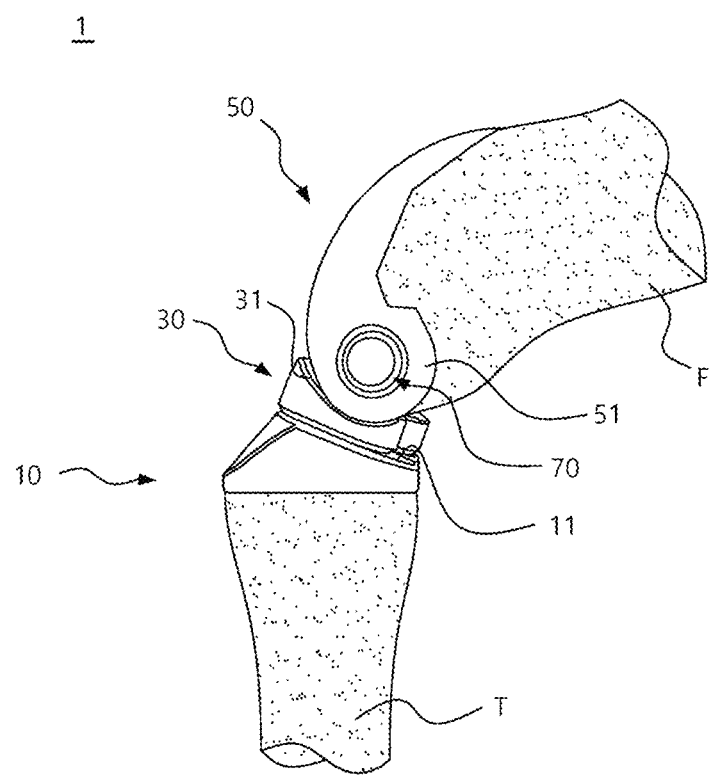
FIG. 23 is a view illustrating the usage state of an animal knee joint implant according to an embodiment of the present disclosure.

FIG. 23 is a view illustrating the usage state of an animal knee joint implant according to an embodiment of the present disclosure. Referring to FIG. 23, the tibia element 10 may be inserted into the proximal portion of an animal's tibia T, the bearing element 30 may be seated on the inclined seating surface 11 of the tibia element 10 to be rotatable, and the femur element 50 may be inserted into the distal portion of the femur F of the animal so that the condyles 51 of the femur element 50 are capable of performing joint motion while being in contact with the joint facet 31 of the bearing element 30. Therefore, it is possible to restore the original anatomical motion of an animal with a damaged knee joint.

The foregoing detailed description is illustrative of the present disclosure. In addition, the foregoing description is intended to illustrate and explain embodiments of the present disclosure, and the present disclosure may be used in various other combinations, modifications, and environments. That is, changes or modifications can be made within the scope of the concept of the present disclosure disclosed herein, the scope equivalent to the content described above, and/or the scope of the skill or knowledge of the art. The embodiments described above are intended to illustrate the best mode for carrying out the technical idea of the present disclosure, and various modifications required for specific application fields and uses of the present disclosure are also possible. Therefore, the foregoing detailed description of the present disclosure is not intended to limit the present disclosure to the disclosed embodiments. In addition, the appended claims should be interpreted as including other embodiments.

The invention claimed is:

1. An animal knee joint implant that reflects an anatomical structure of an animal that is a quadruped, the animal knee joint implant comprising:
   a tibia element configured to be coupled to a proximal portion of a tibia of the animal, the tibial element comprising:
   a tibia contact surface configured to contact with a tibia of the animal;
   a seating surface opposite of the tibia contact surface, the seating surface being a planar surface extending between a medial side of the tibia element and a lateral side of the tibia element, the seating surface being inclined posteriorly and laterally such that a medial height of the tibia element extending between the seating surface and the contact surface at the medial side is higher than a lateral height of the tibia element extending between the seating surface and the contact surface at the lateral side when the contact surface is horizontally disposed;
   a post protruding from the seating surface so as to be perpendicular to the seating surface, the post being inclined laterally and posteriorly when the contact surface is horizontally disposed; and a tibia stem outwardly protruding from the tibia contact surface and being inclined posteriorly when the contact surface is horizontally disposed;

a femur element having medial and lateral condyles; and a bearing element seated on the seating surface of the tibia element and configured to support the medial and lateral condyles of the femur element, the bearing element encircling the post with the bearing element and the seating surface being configured so that the bearing element can freely rotate about the post while being seated directly on the planar seating surface.

2. The animal knee joint implant of claim 1, wherein the post passes through the bearing element so that the bearing element is rotatable about the post on the seating surface of the tibia element.

3. The animal knee joint implant of claim 1, wherein the bearing element comprises a post-receiving hole configured to receive the post of the tibia element so as to rotate about the post.

4. The animal knee joint implant of claim 3, wherein the post-receiving hole has a hole axis perpendicular to a tibia element contact surface.

5. The animal knee joint implant of claim 1, the animal knee joint implant comprising:
the femur element configured to be coupled to a distal portion of a femur of the animal,
wherein the femur element includes a femur stem protruding to be inclined according to the anatomical structure of the animal.

6. The animal knee joint implant of claim 5, wherein the femur stem is inclined medially.

7. The animal knee joint implant of claim 1, the animal knee joint implant comprising:
the femur element configured to be coupled to a distal portion of a femur of the animal; and
a connecting element configured to rotatably connect the femur element on the bearing element.

8. The animal knee joint implant of claim 7, wherein the connecting element includes a yoke unit inserted into a separation space between the medial and lateral condyles of the femur element, and a coupling pin configured to pass through and connect the medial and lateral condyles of the femoral element and the yoke unit.

9. The animal knee joint implant of claim 8, wherein the yoke unit comprises a coupling pin-receiving hole configured to receive the coupling pin and a post-receiving hole configured to receive a post of the tibia element.

10. The animal knee joint implant of claim 9, wherein the coupling pin-receiving hole and the post-receiving hole communicate with each other.

11. The animal knee joint implant of claim 10, wherein the coupling pin includes a gripping groove configured to grip the post so as to prevent the coupling pin from being separated by the post.

12. The animal knee joint implant of claim 1, wherein the seating surface of the tibia element is planar.

13. The animal knee joint implant of claim 1, wherein the medial and lateral condyles of the femur element are disposed on the bearing element.

* * * * *